US00PP14674P29

(12) United States Plant Patent
Davasse

(10) Patent No.: US PP14,674 P2
(45) Date of Patent: Apr. 6, 2004

(54) CARYOPTERIS PLANT NAMED 'MINIBLEU'

(50) Latin Name: *Caryopteris×clandonensis*
Varietal Denomination: Minibleu

(75) Inventor: Jean-Paul Davasse, Angers (FR)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 10/421,348

(22) Filed: Apr. 23, 2003

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Caryopteris plant named 'Minibleu', characterized by its low mounded plant habit; freely branching growth habit; glossy dark green-colored leaves; and numerous violet blue-colored flowers.

1 Drawing Sheet

Botanical classification/cultivar designation: *Caryopteris×clandonensis* cultivar Minibleu.

BACKGROUND OF THE INVENTION

The present Invention relates to a new and distinct cultivar of Caryopteris plant, botanically known as *Caryopteris× clandonensis*, and hereinafter referred to by the name 'Minibleu'.

The new Caryopteris is a product of a open-pollination breeding program conducted by the Inventor in Angers, France. Seed was collected from a population of open-pollinated plants of the *Caryopteris×clandonensis* cultivar Inoveris, not patented, in August, 1997. The cultivar Minibleu was discovered and selected by the Inventor as a flowering plant within the progeny from this open-pollination in a controlled environment in Angers, France.

Asexual reproduction of the new cultivar by softwood cuttings taken at Angers, France since June, 1998, has shown that the unique features of this new Caryopteris are stable and reproduced true to type in successive generations of asexual reproduction.

SUMMARY OF THE INVENTION

The following traits have been repeatedly observed and are determined to be the unique characteristics of 'Minibleu'. These characteristics in combination distinguish 'Minibleu' as a new and distinct cultivar:

1. Low mounded plant habit.
2. Freely branching growth habit.
3. Glossy dark green-colored leaves.
4. Numerous violet blue-colored flowers.

In side-by-side comparisons conducted in Grand Haven, Mich., plants of the new Caryopteris differed from plants of the parent, the cultivar Inoveris, in the following characteristics:

1. Plants of the new Caryopteris had a low mounded plant habit whereas plants of the cultivar Inoveris were taller, more vigorous and more upright in plant habit.
2. Plants of the new Caryopteris had shorter internodes than plants of the cultivar Inoveris.

3. Plants of the new Caryopteris were more densely foliated than plants of the cultivar Inoveris.
4. Plants of the new Caryopteris had darker green-colored leaves than plants of the cultivar Inoveris.
5. Plants of the new Caryopteris were more freely flowering than plants of the cultivar Inoveris.
6. Plants of the new Caryopteris had darker violet blue-colored flowers than plants of the cultivar First Choice.

The new Caryopteris can also be compared to the Caryopteris cultivar, First Choice, disclosed in U.S. Plant Pat. No. 11,958. In side-by-side comparisons conducted in Grand Haven, Mich., plants of the new Caryopteris differed from plants of the cultivar First Choice in the following characteristics:

1. Plants of the new Caryopteris were more freely branching than plants of the cultivar First Choice.
2. Plants of the new Caryopteris were more densely foliated than plants of the cultivar First Choice.
3. Plants of the new Caryopteris had longer and darker green-colored leaves than plants of the cultivar First Choice.
4. Plants of the new Caryopteris were more freely flowering than plants of the cultivar First Choice.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a flowering plant of 'Minibleu'. Flower and foliage colors in the photograph may differ slightly from the color values cited in the detailed botanical description which accurately describe the colors of the new Caryopteris.

DETAILED BOTANICAL DESCRIPTION

The cultivar Minibleu has not been observed under all possible environmental conditions. The phenotype may vary somewhat with variations in environment such as temperature and light intensity, without, however, any variance in genotype. The aforementioned photograph and following observations and measurements describe plants grown in Grand Haven, Mich., under commercial practice in an outdoor nursery during the early fall. Plants used for the photograph and description were about one year old. In the following description, color references are made to The Royal Horticultural Society Colour Chart, 1995 Edition, except where general terms of ordinary dictionary significance are used.

Botanical classification: *Caryopteris×clandonensis* cultivar Minibleu.

Parentage: Seedling resulting from open-pollination of a population of plants of the *Caryopteris×clandonensis* cultivar Inoveris, not patented.

Propagation:

*Type cutting.*—Softwood cuttings.

*Time to initiate roots.*—About 6 to 10 days at 20° C.

*Time to develop roots.*—About 6 to 8 weeks at 20° C.

*Root description.*—Fine; freely branching.

Plant description:

*General appearance.*—Deciduous shrub. Compact and low mounded plant habit.

*Growth and branching habit.*—Freely branching; more than 100 lateral branches develop per plant. Pinching, that is, removal of the terminal apices, enhances branching with lateral branches potentially forming at every node. Moderately vigorous.

*Plant height.*—About 28 cm.

*Plant diameter or spread.*—About 40 cm.

*Lateral branch description.*—Length: About 9 cm. Diameter: About 2 mm. Internode length: About 3 cm. Texture: Slightly pubescent. Color: 187B.

*Foliage description.*—Arrangement: Opposite, simple. Length: About 6 cm. Width: About 1.5 cm. Shape: Lanceolate. Apex: Acute. Base: Cuneate to obtuse. Margin: Occasionally serrate. Texture, upper surface: Smooth, glabrous. Texture, lower surface: Pubescent. Venation pattern: Pinnate. Color: Young and fully expanded foliage, upper surface: 139A; venation, 139A; very glossy. Young and fully expanded foliage, lower surface: 139C; venation, 139C. Petiole: Length: About 5 mm. Diameter: About 1.5 mm. Color, upper and lower surfaces: 139A.

Flower description:

*Flower type and habit.*—Small single campanulate flowers arranged on axillary or terminal panicled cymes. Very freely flowering with about 75 flowers per lateral stem. Flowers last about eight weeks on the plant. Flowers not persistent. Flowers slightly fragrant.

*Flowering season.*—In the garden, flowering is continuous during September and October in Grand Haven, Mich.

*Flower diameter.*—About 5 mm.

*Flower depth.*—About 1 cm.

*Flower buds.*—Length: About 3 mm. Diameter: About 1.5 mm. Shape: Ovoid. Color: 95A.

*Petals.*—Quantity/arrangement: Five per flower fused at base; one larger petal than the other four petals. Petal length: Four smaller petals, about 3 mm; larger petal, about 5 mm. Petal width: Four smaller petals, about 2 mm; larger petal, about 4 mm. Shape: Roughly spatulate. Apex: Four smaller petals, obtuse; larger petal, lacerate. Margin: Four smaller petals, entire; larger petal, fringed. Texture, upper and lower surfaces: Glabrous, smooth. Color: When opening, upper and lower surfaces: 95A. Fully opened, upper surface: 95A to 95B. Fully opened, lower surface: 95A.

*Sepals.*—Quantity/arrangement: Five to six, fused; campanulate. Calyx length: About 4 mm. Calyx diameter: About 2 mm. Shape: Lanceolate. Apex: Acute. Margin: Entire. Texture, upper and lower surfaces: Slightly pubescent. Color, upper and lower surfaces: 138B overlain with 95A.

*Pedicels.*—Length: About 3 mm. Diameter: Less than 1 mm. Strength: Strong. Angle to stem: About 30° from vertical. Color: 139A.

*Reproductive organs.*—Stamens: Quantity: Four per flower. Anther shape: Elliptic. Anther length: About 0.5 mm. Anther color: Close to 202B. Pollen amount: Scarce. Pollen color: 202D. Pistils: Quantity: One per flower. Pistil length: About 1 cm. Stigma color: 101C. Style length: About 9 mm. Style color: 101C. Ovary color: 145A. Seeds: Length: About 0.5 mm. Diameter: About 0.5 mm. Color: 145A.

Disease/pest resistance: Plants of the new Caryopteris have not been observed to be resistant to pathogens and pests common to Caryopteris.

It is claimed:

1. A new and distinct cultivar of Caryopteris plant named 'Minibleu', as illustrated and described.

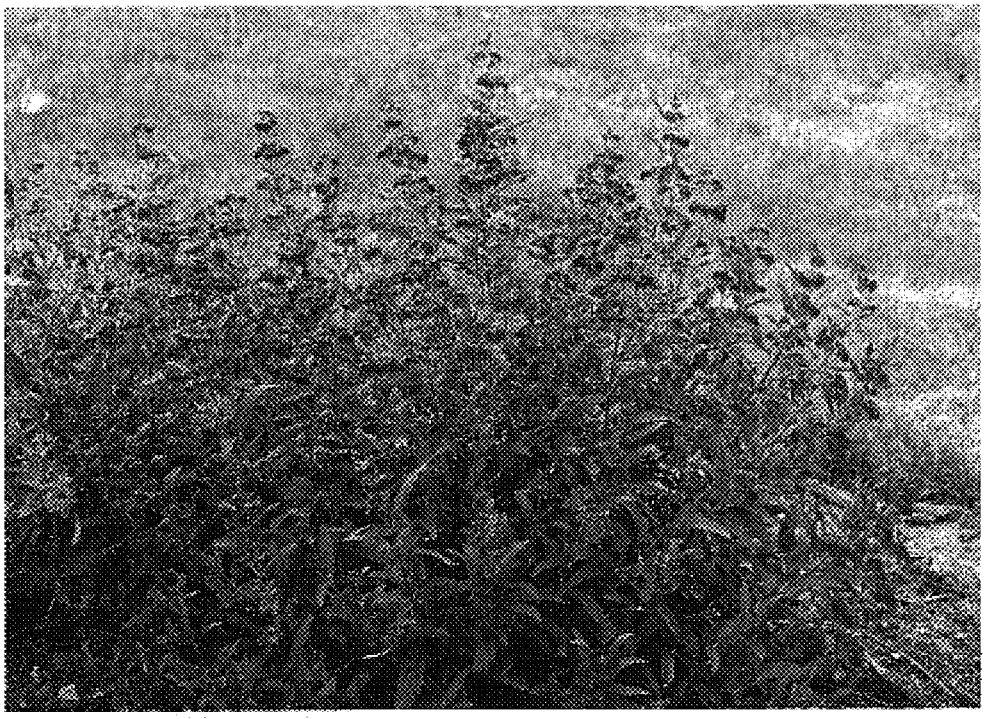

* * * * *